United States Patent [19]
Stauffer

[11] 3,963,573
[45] June 15, 1976

[54] PROCESS FOR PRODUCING N-ACYL-L-METHIONINE

[75] Inventor: Clyde Eugene Stauffer, Cincinnati, Ohio

[73] Assignee: The Procter & Gamble Company, Cincinnati, Ohio

[22] Filed: Mar. 3, 1975

[21] Appl. No.: 554,947

[52] U.S. Cl. .................................. 195/29; 195/2
[51] Int. Cl.$^2$ .......................................... C12B 1/00
[58] Field of Search ................... 195/4, 29, 68, 2

[56] References Cited
UNITED STATES PATENTS
2,511,867   6/1950   Neuberg et al. .................. 195/29

OTHER PUBLICATIONS
Brenner et al., "A Simple Enzymatic Method for the Preparation of D and L Methionine" Helv. Chim. Acta. 32 pp. 333–337 (1949).

Perlman et al., "Methods in Enzymology" vol. XIX Proteolytic Enzymes Academic Press 1970 pp. 226–244 and pp. 199–215.

*Primary Examiner*—A. Louis Monacell
*Assistant Examiner*—R. B. Penland
*Attorney, Agent, or Firm*—Jerry J. Yetter; Julius P. Filcik; Richard C. Witte

[57] ABSTRACT

A process for producing optically pure N-acyl-L-methionine comprising (1) subjecting an N-acyl-D,L-methionine ester to the action of a proteolytic enzyme selected from the group consisting of sulfhydryl proteinases and microbially derived serine proteinases; and (2) separating the resulting N-acyl-L-methionine. The N-acyl group can be chemically removed to provide L-methionine.

9 Claims, No Drawings

PROCESS FOR PRODUCING N-ACYL-L-METHIONINE

BACKGROUND OF THE INVENTION

1. Field of the Invention

This invention relates to a process for providing N-acyl-L-methionine and L-methionine.

2. The Prior Art

Heretofore it was known that N-acyl-D,L-methionine could be separated into its optical antipodes by reacting it with certain optically active bases, for example, threo-2-amino-(p-methylsulfonylphenyl)-1,3-propanediol, brucine, fenchylamine or lysine and to separate diastereomer salts from each other on the basis of their different physical properties, especially their different solubilities. (See, for example, U.S. Pat. No. 3,845,110 issued Oct. 29, 1974 to Fahnenstich et al.) These optically active bases, however, are themselves difficult to obtain. In addition, such processes generally do not provide good yields of high purity N-acyl-L-methionine.

Heretofore, enzymes which selectively act on particular amino acid derivatives have been employed to provide optically active amino acids. For example, U.S. Pat. No. 3,386,888, issued June 4, 1968 to Chibata et al. discloses that L-methionine can be recovered by action of acylase on N-acyl-D,L-methionine. This enzymatic method, however, is not completely desirable. The acylase employed is expensive; the rate at which the reaction proceeds is relatively slow; and acylase enzyme is unstable.

The action of pancreas extract (which contains a mammalian derived serine proteinase) on D,L-methionine isopropyl ester can provide at least a partial resolution of methionine. See, Brenner, et al., Helv. Chim. Acta, Vol. 32, pages 333–37 (1949), and Wretlind, Acta physiol. Scan., Vol. 20, page 1 (1950). Mammalian derived enzymes, however, are expensive and these publications suggest that good optical purity is not obtained. These publications, therefore, do not suggest a commercially desirable process for providing L-methionine.

It is known that microbially derived serine proteinases, for example, Novo and Carlsberg subtilisins, exhibit varying degrees of esterase activity on various N-acyl-L-amino acid esters. See, for example, Barel et al., The Jour. of Biolog. Chem., Vol. 243, pages 1344–48 (1968) and Morihara et al., Arch. Biochem. and Biophy., Vol. 129, pages 620–633 (1969). These publications show that serine proteinases exhibit high esterase activity on some of these amino acid derivatives and little or no esterase activity on others depending on the particular amino acid. These publications do not disclose the activity of serine proteinases on N-acyl-L-methionine esters, or the activity of serine proteinases on racemic N-acyl-D,L-amino acid esters.

Both L-methionine and N-$C_{1-9}$ acyl-L-methionine are valuable nutritional supplements, therefore a more effective process for obtaining these nutritionally valuable compounds would be very desirable. An especially effective process would (1) involve readily available and inexpensive materials (e.g. enzymes), and (2) produce high purity material in high yield at a rapid rate.

SUMMARY OF THE INVENTION

This invention provides an especially effective process for obtaining N-$C_{1-9}$ acyl-L-methionine and L-methionine. In summary, this invention involves a process for producing optically pure N-acyl-L-methionine comprising (1) subjecting N-acyl-D,L-methionine ester to the action of a proteolytic enzyme selected from the group consisting of (a) sulfhydryl proteinases, and (b) microbially derived serine proteinases; and (2) separating the resulting N-acyl-L-methionine. In another aspect of this invention the N-acyl group can be chemically removed to provide L-methionine.

DETAILED DESCRIPTION OF THE INVENTION AND ITS PREFERRED EMBODIMENTS

This invention relates to a process for producing optically pure N-acyl-D,L-methionine comprising (1) subjecting N-acyl-D,L-methionine ester to the action of a proteolytic enzyme selected from the group consisting of (a ) sulfhydryl proteinases, and (b) microbially derived serine proteinases; and (2) separating the resulting N-acyl-L-methionine.

As used herein "optically pure N-acyl-L-methionine" means N-acyl-L-methionine substantially free of the D-isomer.

It has been found that certain readily available proteinases, namely, sulfhydryl proteinases and microbially derived serine proteinases exhibit high esterase activity for N-acyl-L-methionine esters, and very low esterase activity for N-acyl-D-methionine esters. Furthermore, it has been found that the high esterase activity exhibited for the L-isomer is not inhibited by the presence of the D-isomer. Subjecting N-acyl-D,L-methionine ester to the action of such a proteinase provides a mixture of N-acyl-D-methionine ester and N-acyl-L-methione. The N-acyl-L-methionine can be readily separated from the mixture by conventional means, for example, by adjusting the pH of an aqueous mixture and extracting with an organic solvent such as chloroform, ethyl acetate or butyl acetate.

A variety of specific N-acyl-D,L-methionine ester compounds can be employed in this invention. Preferable compounds will have the acyl and ester groups mentioned below.

Preferably the acyl group is derived from fatty acids containing from 1 to 9 carbon atoms. More particularly, the N-acyl group will preferably be formyl, acetyl, propionoyl, butyroyl, valeroyl, caproyl, enanthoyl, caprylyl, or pelargonoyl. The ester group can be derived from a variety of alcohols containing from 1 to 10, preferably 1 to 6, carbon atoms. Especially suitable examples of ester groups are methyl, ethyl, n-propyl, isopropyl, n-butyl, sec. butyl and isobutyl. Especially suitable examples of acyl groups are formyl, acetyl and propionyl. Racemic N-acetyl-D,L-methionine methyl ester is most preferred for use in the process of this invention.

Suitable sulfhydryl proteinases are, for example, papain, ficin and bromelain.

Serine proteinases suitable for use in this invention are derived from microorganisms such as bacteria, fungi and mold. Microbially derived serine proteinases are preferred for use in the process of this invention. These proteinases are relatively inexpensive and commercially available.

An example of preferred serine proteinases for use in this invention are those derived from the bacterial organism *Bacillus subtilis* and termed subtilisins.

A preferred subtilisin of the present invention is the *Bacillus subtilis*-derived Carlsberg strain. The Carlsberg strain employed in accordance with the present invention is a known subtilisin train, the amino acid sequence of which is described in Smith et al., "The Complete Amino Acid Sequence of Two Types of Subtilisin, BPN' and Carlsberg," J. of Biol. Chem. volume 241, Dec. 25, 1966, at page 5974. This subtilisin strain is characterized by a tyrosine to tryptophan ratio of about 13:1. The above reference including its description of the amino acid sequence of the Carlsberg subtilisin is hereby incorporated by reference.

An X-ray mutated *Bacillus subtilis*-derived subtilisin constitutes another preferred subtilisin of the present invention. This mutation can be effected in accordance with U.S. Pat. No. 3,031,380 issued Apr. 24, 1962 to Minagawa et al. by irradiation of a *Bacillus subtilis* organism with X-rays. Subsequent treatment in a conventional manner can be employed to result in the preparation of an enzymatic composition. The patent describes a process whereby an enzymatic composition is produced by subjecting *Bacillus subtilis* to X-rays of an intensity coresponding substantially to 24–50 roentgens for an interval of at least half an hour, selecting from the colony thus subject to X-rays a strain identified by cells having hairless, rough, jagged, spotted and dull white characteristics, separating said strain and placing the separated strain in a culture selected from the group consisting of wheat bran and corn meal, maintaining the culture for a period of at least 40 hours while aerating the culture substantially continuously, and drying the culture. The disclosure of U.S. Pat. No. 3,031,380 is hereby incorporated by reference.

Other examples of suitable serine proteinases for use herein include the following. Serine proteinases derived from *Aspergillus oryzae*. Methods for producing and separating these mold derived enzymes are known to those skilled in the art. See, for example, Subramamian et al., Biochemistry, Vol. 3, No. 12, pages 1861–74 (1964), and Misaki et al., Agr. Biol. Chem., Vol. 34, No. 9, pages 1383–92 (1970). Serine proteinase derived from *Streptomyces griseus* (ATCC 3463). Such serine proteinases are available commercially under the tradename "Pronase" from Kaken Chemical Co., Japan. Methods for producing and separating the proteinases are known. See, for example, Narahashi et al., The Journal of Biochemistry, Vol. 62, No. 6, pages 633–41 (1967). Serine proteinase derived from *Aspergillus sydowi*. Methods for producing and separating this fungally derived serine proteinase are known. See, for example, Danno et al., Agr. Biol. Chem., Vol. 31, No. 10, pages 1151–58 (1967).

Other suitable examples of microbially derived serine proteinases are Aspergillus alkaline proteinase (E.C. 3.4 21.15), Alternaria endopeptidase (E.C. 3.4.21.16), Arthrobacter serine proteinase (E.C. 3.4.21.17). These particular enzymes have been identified according to a systematic nomenclature involving an "E.C. number". See "Enzyme Nomenclature", Commission of Biochemical Nomenclature, Elsevier Publishing Company (1973), U.S. Library of Congress Card. No. 73-78247.

The action of the proteolytic enzyme on the N-acyl-D,L-methionine ester is very suitably conducted in an aqueous medium maintained at a pH of from about 5 to about 10, preferably about 7 to 8, and at a temperature of from about 10° to about 60°C. Preferably the temperature is maintained in the range of from about 20° to 40°C.

Because of the high selective esterase activity of the particular proteolytic enzymes employed in this invention toward N-acyl-L-methionine ester in N-acyl-D,L-methionine ester mixtures very small amounts of the proteolytic enzyme are required in order to rapidly produce N-acyl-L-methionine. For example, aqueous solutions containing from about 0.0005% to 1.0%, by weight, preferably from about 0.005% to 0.5%, by weight, of enzymes are employed. (Amounts of enzyme referred to herein refer to pure crystalline enzyme.)

The amount of N-acyl-D,L-methionine employed will generally be at least about 5%, by weight, of the aqueous solution. Preferably larger amounts are employed, for example, amounts up to and exceeding the maximum solubility of the N-acyl-D,L-methionine ester in the aqueous medium. (Amounts exceeding maximum solubility can be employed since as the L-ester is consumed by the action of the enzyme more will enter solution.)

The rate of the action of the enzyme on the material will depend on the concentration of the enzyme and ester in solution. In this regard, N-acetyl-D,L-methionine methyl ester is quite suitable in that it exhibits good solubility in water (about 20%, by weight, at pH 7.5 and 25°C).

Since N-acetyl-D,L-methionine methyl ester is a preferred ester substrate of this invention, a detailed specific embodiment of the invention employing this material is provided in Example I.

EXAMPLE I

Part A. Preparation of N-acetyl-D,L-methionine methyl ester.

One hundred grams of D,L-methionine were mixed with 500 ml. of methanol containing 30 g NaOH to form a stirrable slurry. To this mixture there was slowly added with stirring 1.5 mole equivalents (based on D,L-methionine) of acetic anhydride. This mixture was continuously stirred until the slurry turned to a clear solution. The resulting clear solution contained N-acetyl-D,L-methionine dissolved in methanol.

To this solution was added with stirring sufficient anhydrous $H_2SO_4$ to neutralize the NaOH and render the solution slightly acidic. Under these conditions the N-acetyl-D,L-methionine was converted to N-acetyl-D,L-methionine methyl ester. The remaining methanol and methyl acetate (formed from the reaction of residual acetic acid and acetic anhydride with NaOH) was removed by warming the mixture under vacuum. The remaining mixture was slurried with chloroform and filtered to removed sodium sulfate salts. The ester-chloroform solution was then water washed to remove any remaining salts. The resulting ester-chloroform solution was then warmed under vacuum to remove the chloroform. The resulting material was N-acetyl-D,L-methionine methyl ester.

Part B. Preparation of N-acetyl-L-methionine.

An aqueous solution containing 20%, by weight, N-acetyl-D,L-methionine methyl ester was formed. The pH was adjusted to about 7.5 by the addition of 1N NaOH. To this solution there was slowly added 0.04%, by weight of the aqueous solution, of crystalline subtilisin Carlsberg, a serine proteinase commercially available under the tradename "Alcalase". During the addition of the proteinase, the solution was continuously stirred, and the pH was kept constant by the automatic addition of 1N NaOH from an automatic titrator. (The titrator was a commonly available Radiometer pH-stat type.) When no further addition of NaOH is needed to maintain pH, the reaction is complete. (In this case time was about 30 minutes.)

The resulting mixture of N-acetyl-D-methionine methyl ester and N-acetyl-L-methionine were separated in the following manner. The aqueous mixture was raised to a pH of 10–11 by the addition of NaOH. This aqueous mixture was then extracted with chloroform in the following manner. To the mixture was added an equal volume of chloroform. The resulting mixture agitated briefly. The water immiscible chloroform was then allowed to separate into a discrete layer. The water and chloroform layers were then separated. The chloroform extraction procedure was repeated two additional times.

The separated chloroform layers containing N-acetyl-D-methionine methyl ester were combined. The chloroform was removed by warming the chloroform solution under vacuum. The resulting N-acetyl-D-methionine methyl ester can be added to water or methanol containing NaOH, and heated for a time sufficient to racemize the ester material. The resulting D,L-material can then be recycled in the process.

The water layer, containing N-acetyl-L-methionine, was acidified by the addition of $H_2SO_4$ to lower the pH to 2 or less. This acidified water was then extracted with chloroform in the following manner. An equal volume of chloroform was added to the acidified water and briefly agitated. The chloroform was allowed to separate from the water to form two discrete layers. The chloroform layer was separated from the water layer. This chloroform extraction procedure was repeated two additional times.

The separated chloroform layers were combined. The chloroform solution was then warmed gently under vacuum to remove the chloroform. The product was N-acetyl-L-methionine having an optical purity of better than 95%.

While this example presents a comprehensive procedure for obtaining N-acetyl-L-methionine, it should be understood that a variety of methods are available to those skilled in the art forming N-acyl-D,L-methionine esters, and a variety of methods are available for separating mixtures of N-acyl-D-methionine esters and N-acyl-L-methionine.

EXAMPLE II

When in Example I, Part B, the serine proteinase employed in subtilisin BPN, BPN', or *Aspergillus oryzae* derived proteinase, the same or similar results are obtained in that N-acetyl-L-methionine is rapidly produced, N-acetyl-D-methionine methyl ester is unaffected, and the two compounds can be readily separated to provide optically pure N-acetyl-L-methionine.

EXAMPLE III

When in Example I, Part B, the D,L-ester material employed is a methyl, ethyl, propyl, or isopropyl ester of N-formyl-D,L-methionine; an ethyl, propyl, or isopropyl ester of N-acetyl-D,L-methionine; a methyl, ethyl, propyl, or isopropyl ester of N-propionyl-D,L-methionine; the same or similar results are obtained in that an optically pure N-(formyl, acetyl or propionyl) L-methionine is produced which can be separated from the N-(formyl, acetyl or propionyl)-D-methionine ester material.

EXAMPLE IV

When in Example I, papin or ficin, sulfhydryl proteinases, are employed instead of the serine proteinase, substantially the same results are obtained in that optically pure N-acetyl-L-methionine is produced.

The N-acyl-L-methionine provided by the process of the invention can be converted to L-methionine in a simple manner. For example, it can be treated at elevated temperatures with dilute acid; for example, it can be dissolved in 2N hydrochloric acid and this solution warmed for a time to about 80° to 100°C.

L-methionine is a known and useful item of commerce. $N-C_{1-9}$ acyl-L-methionines are especially useful in supplementing sulfur amino acid deficient protein foods as disclosed in U.S. Patent application Ser. No. 256,860 filed May 25, 1972, now U.S. Pat. No. 3,878,305. For this reason, $N-C_{1-9}$ acyl-L-methionine, especially N-formyl-L-methionine, N-acetyl-L-methionine and N-propionyl-L-methionine are preferred products of the process of this invention.

What is claimed is:

1. A process for producing optically pure N-acyl-L-methionine comprising:
    1. subjecting a mixture of N-acyl-L-methionine ester and N-acyl-D-methionine ester to the action of a proteolytic enzyme selected from the group consisting of microbially derived serine proteinases; and
    2. separating the resulting N-acyl-L-methionine from the unreacted N-acyl-D-methionine ester.

2. The process of claim 1 wherein the acyl group contains from 1 to 9 carbon atoms.

3. The process of claim 2 wherein the ester group contains from 1 to 10 carbon atoms.

4. The process of claim 1 wherein the proteolytic enzyme is a microbially derived serine proteinase which is a member selected from the group consisting of subtilisin Carlsberg and subtilisin BPN.

5. The process of claim 1 wherein the mixture of N-acyl-L-methionine ester and N-acyl-D-methionine ester comprises N-acetyl-D,L-methionine methyl ester.

6. A process according to claim 1 for preparing optically pure N-acetyl-L-methionine comprising:
    1. subjecting an aqueous solution of a mixture of N-acetyl-D-methionine methyl ester and N-acetyl-L-methionine methyl ester to the action of a proteolytic enzyme which is a member selected from the group consisting of the microbially derived serine proteinases, at a pH in the range of from 5 to 10; and
    2. separating the resulting N-acetyl-L-methionine.

7. A process according to claim 6 which is carried out at a pH in the range from about 7 to 8 and at a temperature in the range from about 10°C to about 60°C.

8. A process according to claim 7 wherein the serine proteinase is a member selected from the group consisting of subtilisin Carlsberg and subtilisin BPN.

9. A process according to claim 8 wherein the proteinase is subtilisin Carlsberg and the temperature is in the range from 20°C to 40°C.

* * * * *